United States Patent
Hubelbank

(10) Patent No.: US 6,668,182 B2
(45) Date of Patent: Dec. 23, 2003

(54) PULSE OXYMETRY DATA PROCESSING

(75) Inventor: Mark Hubelbank, Sudbury, MA (US)

(73) Assignee: Northeast Monitoring, Sudbury, MA (US)

(*) Notice: Subject to any disclaimer, the term of this patent is extended or adjusted under 35 U.S.C. 154(b) by 62 days.

(21) Appl. No.: 10/044,135

(22) Filed: Jan. 10, 2002

(65) Prior Publication Data

US 2003/0130584 A1 Jul. 10, 2003

(51) Int. Cl.[7] .................................. A61B 5/00
(52) U.S. Cl. ........................... 600/323; 600/336
(58) Field of Search ......................... 600/309–310, 600/322–323, 336

(56) References Cited

U.S. PATENT DOCUMENTS

| | | | |
|---|---|---|---|
| 5,343,869 A | | 9/1994 | Pross et al. |
| RE35,122 E | * | 12/1995 | Corenman et al. ........... 600/324 |
| 5,579,775 A | | 12/1996 | Dempsey et al. |
| 5,606,978 A | | 3/1997 | Armstrong et al. |
| 5,645,068 A | | 7/1997 | Mezack et al. |
| 5,678,562 A | | 10/1997 | Sellers |
| 5,924,980 A | * | 7/1999 | Coetzee ....................... 600/300 |
| 6,125,296 A | | 9/2000 | Hubelbank |
| 6,342,039 B1 | * | 1/2002 | Lynn et al. .................. 600/529 |

FOREIGN PATENT DOCUMENTS

| | | |
|---|---|---|
| EP | 0 553 372 | 8/1993 |
| EP | 0 518 073 | 3/1997 |

OTHER PUBLICATIONS

Detailed overview of the PC Card Standard, PCMCIA, retrieved from Internet, Jan. 24, 2000, <URL: http://www.pcmcia.org/pccardstandard.htm>.

* cited by examiner

Primary Examiner—Eric F. Winakur
Assistant Examiner—Matthew Kremer
(74) Attorney, Agent, or Firm—Fish & Richardson PC

(57) ABSTRACT

In one aspect, the invention is a method for processing pulse oxymetry data signals. The method includes recording pulse oxymetry data signals. The pulse oxymetry data signals have a plurality of oxymetry waveforms. The method also includes determining a correlation coefficient between sequential oxymetry waveforms and identifying a valid pulse oxymetry waveform.

27 Claims, 9 Drawing Sheets

PULSE OXYMETRY DATA PROCESSING

The present invention relates in general to electrocardiographic (ECG) and oxygen saturation signal recording and more particularly concerns a novel technique for processing the ECG and oxygen saturation signals.

BACKGROUND OF THE INVENTION

For background on ECG and oxygen saturation signal recording reference is made to U.S. Pat. No. 6,125,296.

A typical prior art approach for measuring oxygen saturation uses either a large nonportable bedside unit or a portable unit with recording capability.

An object of this invention is to provide an automatic mechanism for identifying those portions of the recorded pulse oxymetry data signals that are invalid.

Another object of the invention is to use pulse oxymetry data signals, which this invention determines as valid, and identify those segments of the data signals that are valid desaturation signals.

BRIEF SUMMARY OF THE INVENTION

In one aspect, the invention is a method for processing pulse oxymetry data signals. The method includes recording pulse oxymetry data signals. The pulse oxymetry data signals have a plurality of oxymetry waveforms. The pulse oxymetry data signals correspond to oxygen saturation data signals. The method also includes determining a correlation coefficient between sequential oxymetry waveforms and identifying a valid pulse oxymetry waveform.

This aspect of the invention may have one or more of the following features. Determining the correlation coefficient includes storing a first pulse oxymetry waveform segment having a first length in a first buffer, copying the first pulse oxymetry waveform segment from the first buffer to a second buffer, copying a second pulse oxymetry waveform segment having a second length to the first buffer, comparing the first length, the second length and a predetermined value, and determining a correlation length related to the first and second lengths and the predetermined value. Determining a correlation length includes taking the minimum of the first length, the second length, and the predetermined value. Determining a correlation coefficient includes determining a correlation coefficient from the first pulse oxymetry waveform segment and the second pulse oxymetry waveform segment, comparing the correlation coefficient to a threshold value, and filtering out an invalid pulse oxymetry waveform segment that has a correlation coefficient below the threshold value. Filtering out the invalid pulse oxymetry waveform segment includes eliminating pulse oxymetry waveform segments if 75% of the correlation coefficients for the last 6 seconds are above the threshold value of 0.9. The method also includes determining valid oxygen desaturation data signals. Determining valid desaturation signals comprises labeling oxygen saturation signals below a threshold value for a predetermined time as valid desaturation data. The threshold value is 88% and the predetermined time is 300 seconds. Determining valid desaturation signals comprises eliminating artifacts. Determining valid desaturation signals comprises ignoring desaturation signals below the threshold value that do not reach a peak value.

In another aspect, the invention is an apparatus for processing pulse oxymetry data signals. The apparatus includes a memory that stores executable instruction data signals and a processor. The processor executes the instruction data signals to record the pulse oxymetry data. The pulse oxymetry data has a plurality of oxymetry waveforms. The pulse oxymetry data signals correspond to oxygen saturation data signals. The processor also executes the instruction data signals to determine a correlation coefficient between sequential oxymetry waveforms and to identify invalid pulse oxymetry waveforms.

This aspect of the invention may have one or more of the following features. Determining the correlation coefficient includes storing a first pulse oxymetry waveform segment having a first length in a first buffer, copying the first pulse oxymetry waveform segment from the first buffer to a second buffer, copying a second pulse oxymetry waveform segment having a second length to the first buffer, comparing the first length, the second length and a predetermined value, and determining a correlation length related to the first and second lengths and the predetermined value. Determining a correlation length includes taking the minimum of the first length, the second length, and the predetermined value. Determining a correlation coefficient includes determining a correlation coefficient from the first pulse oxymetry waveform segment and the second pulse oxymetry waveform segment, comparing the correlation coefficient to a threshold value, and filtering out an invalid pulse oxymetry waveform segment that has a correlation coefficient below the threshold value. Filtering out the invalid pulse oxymetry waveform segment includes eliminating pulse oxymetry waveform segments if 75% of the correlation coefficients for the last 6 seconds are above the threshold value of 0.9. The processor also executes the instruction data signals to determine valid oxygen desaturation data signals. Determining valid desaturation signals comprises labeling oxygen saturation signals below a threshold value for a predetermined time as valid desaturation data. The threshold value is 88% and the predetermined time is 300 seconds. Determining valid desaturation signals comprises eliminating artifacts. Determining valid desaturation signals comprises ignoring desaturation signals below the threshold value that do not reach a peak value.

In still another aspect, the invention is an article that includes a machine-readable medium that stores executable instruction signals for processing pulse oxymetry data signals. The instruction signals cause a machine to record the pulse oxymetry data signals. The pulse oxymetry data signals have a plurality of oxymetry waveforms. The pulse oxymetry data signals correspond to oxygen saturation data signals. The instructions also cause a machine to determine a correlation coefficient between sequential oxymetry waveforms and to identify invalid pulse oxymetry waveforms.

This aspect of the invention may have one or more of the following features. Determining the correlation coefficient includes storing a first pulse oxymetry waveform segment having a first length in a first buffer, copying the first pulse oxymetry waveform segment from the first buffer to a second buffer, copying a second pulse oxymetry waveform segment having a second length to the first buffer, comparing the first length, the second length and a predetermined value, and determining a correlation length related to the first and second lengths and the predetermined value. Determining a correlation length includes taking the minimum of the first length, the second length, and the predetermined value. Determining a correlation coefficient includes determining a correlation coefficient from the first pulse oxymetry waveform segment and the second pulse oxymetry waveform segment, comparing the correlation coefficient to a threshold value, and filtering out an invalid pulse oxymetry waveform segment that has a correlation coefficient below the threshold value. Filtering out the invalid pulse oximetry waveform segment includes eliminating pulse oximetry waveform segments if 75% of the correlation coefficients for the last 6 seconds are above the threshold value of 0.9. The instructions also cause a machine to determine valid oxygen desaturation data signals. Determining valid desaturation signals comprises labeling oxygen saturation signals below a threshold value for a predetermined time as valid desaturation data. The threshold value is 88% and the predetermined time is 300 seconds. Determining valid desaturation signals comprises eliminating artifacts. Determining valid desaturation signals comprises ignoring desaturation signals below the threshold value that do not reach a peak value.

Some or all of the aspects of the invention described above may have some or all of the following advantages. The invention makes it impossible to automatically differentiate valid oxymetry data signals from invalid oxymetry data signals. The invention also automatically determines true desaturation signals from invalid desaturation signals.

Other features, objects and advantages will become apparent from the following detailed description when read in connection with the accompanying drawing in which:

DETAILED DESCRIPTION

Typically, an oxygen sensor is used to record pulse oxymetry signals. The oxygen sensor provides a signal representative of oxygen saturation. The oxygen sensor is applied to a finger or ear lobe. However, pulse oximetry measurements are sensitive to patient movement. Small movements of the sensor can produce invalid data signals, which is difficult and time consuming for a user to discern.

It is especially difficult for the user to identify periods of desaturation in the data from false desaturation data. Desaturation periods are marked by low values of blood oxygen saturation. Desaturation can be caused by emphysema, blockages of the airways (e.g., snoring), etc. In many cases, it is difficult or impossible to differentiate a true desaturation from the invalid data signals by looking at the oxygen saturation data signals alone.

Figure 1:
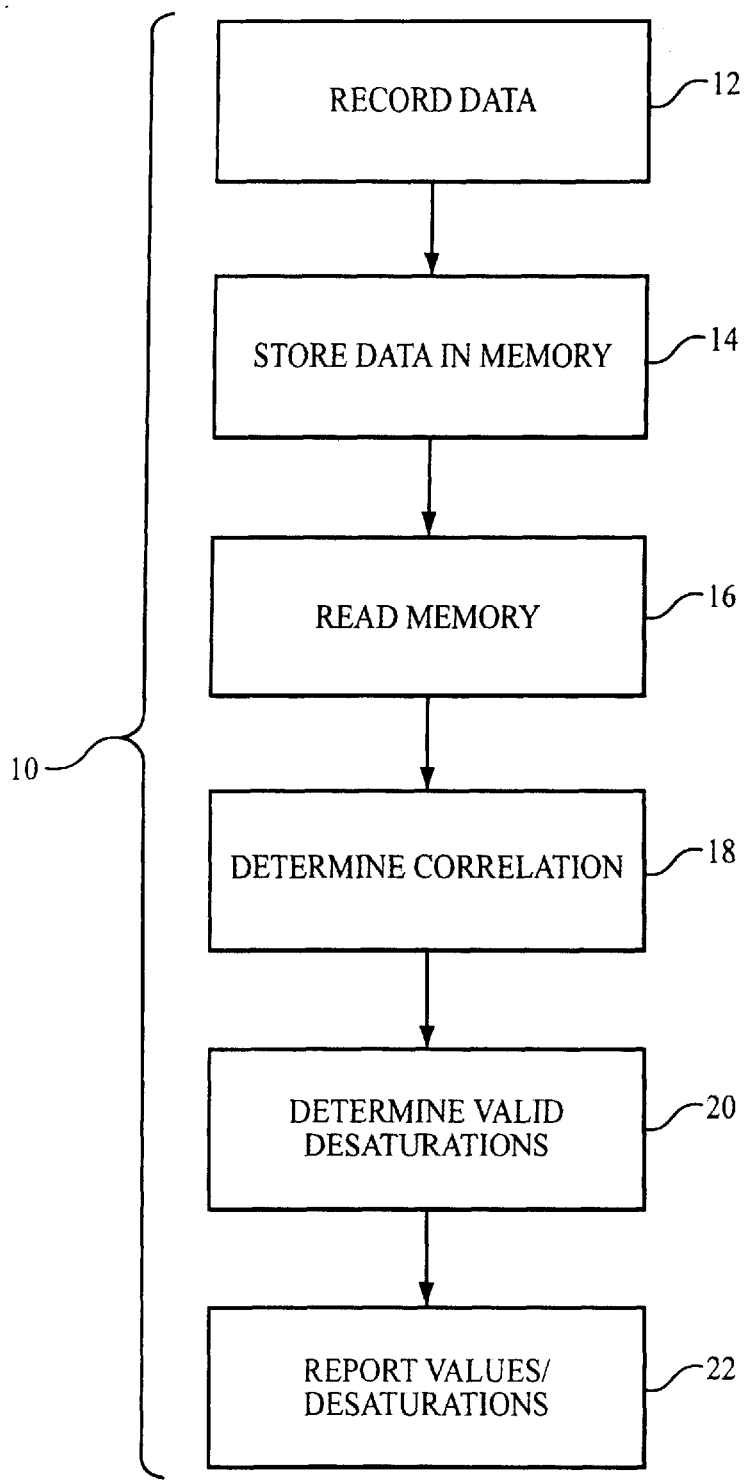
FIG. 1 is a flowchart of a process for processing pulse oxymetry data signals.
Figure 2:
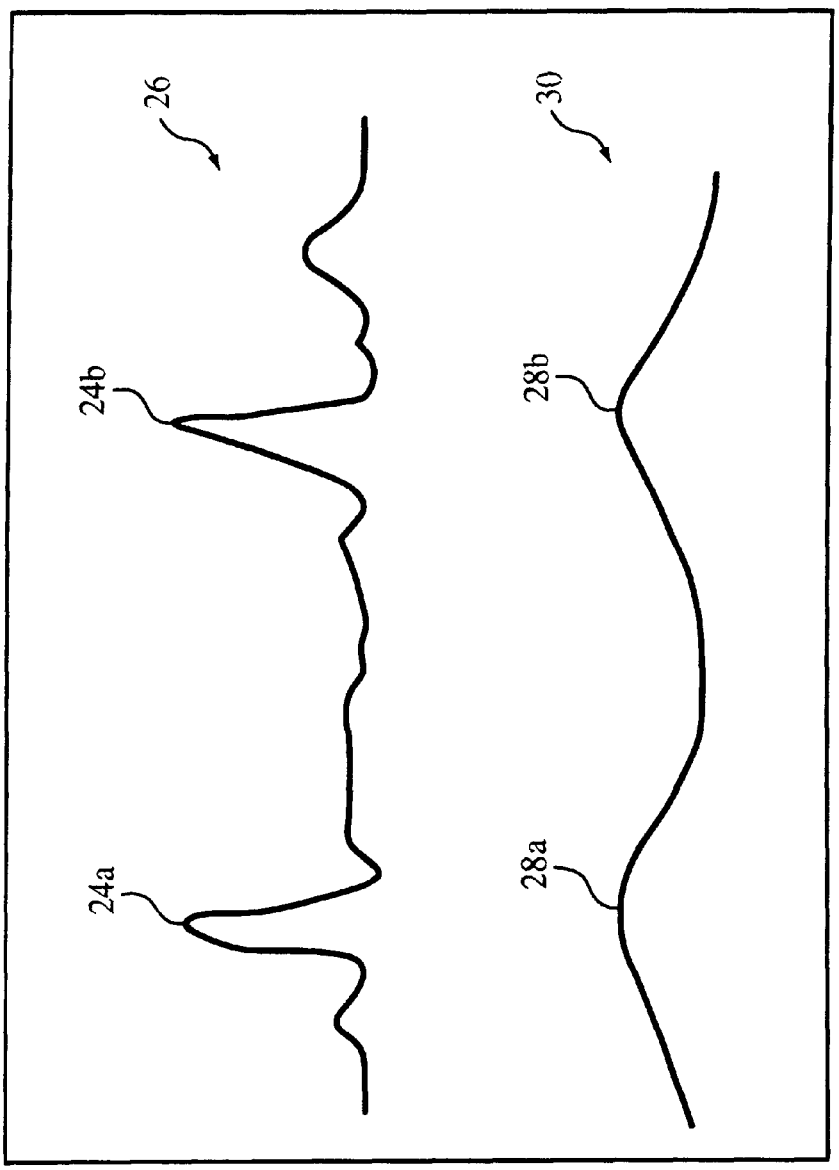
FIG. 2 is a graph of a pulse signal and a corresponding pulse oxymetry signal.

Referring to FIGS. 1 and 2, a process 10 automatically (i.e., without user intervention) determines invalid oxymetry data signals recorded from an electrocardiographic and oxygen saturation signal. Process 10 determines a cross-correlation coefficient between two adjacent pulse oxymetry waveforms and compares it to a predetermined value. Every pulse oxymetry waveform corresponds to a pulse wave having a series of R-waves 24 (e.g., first R-wave 24a and second R-wave 24b). R-waves 24 are a depolarization of the apex of the heart whereby most of the ventricle is activated. R-waves 24 are represented by an upward deflection on a pulse signal 26. R-waves 24 are used to identify the beginning of a pulse oxymetry waveform 28 (e.g., first pulse oxymetry waveform 28a and second pulse oxymetry waveform 28b) in the pulse oxymetry data signal 30. For example, first R-wave 24a corresponds to first pulse oxymetry waveform 28a and second R-wave 24b corresponds to second pulse oxymetry waveform 28b. Process 10 keeps those successive oxymetry waveforms that have a cross-correlation coefficient above the predetermined value. The valid oxymetry data signals are further reviewed to determine if the oxygen desaturation signal values are also valid. By automatically filtering-out erroneous and invalid oxymetry data signal, a physician has a better understanding of the condition of a patient to make a better diagnosis faster than having the physician sift through the recorded oxymetry data signals looking for false recorded data signals.

Figure 3:
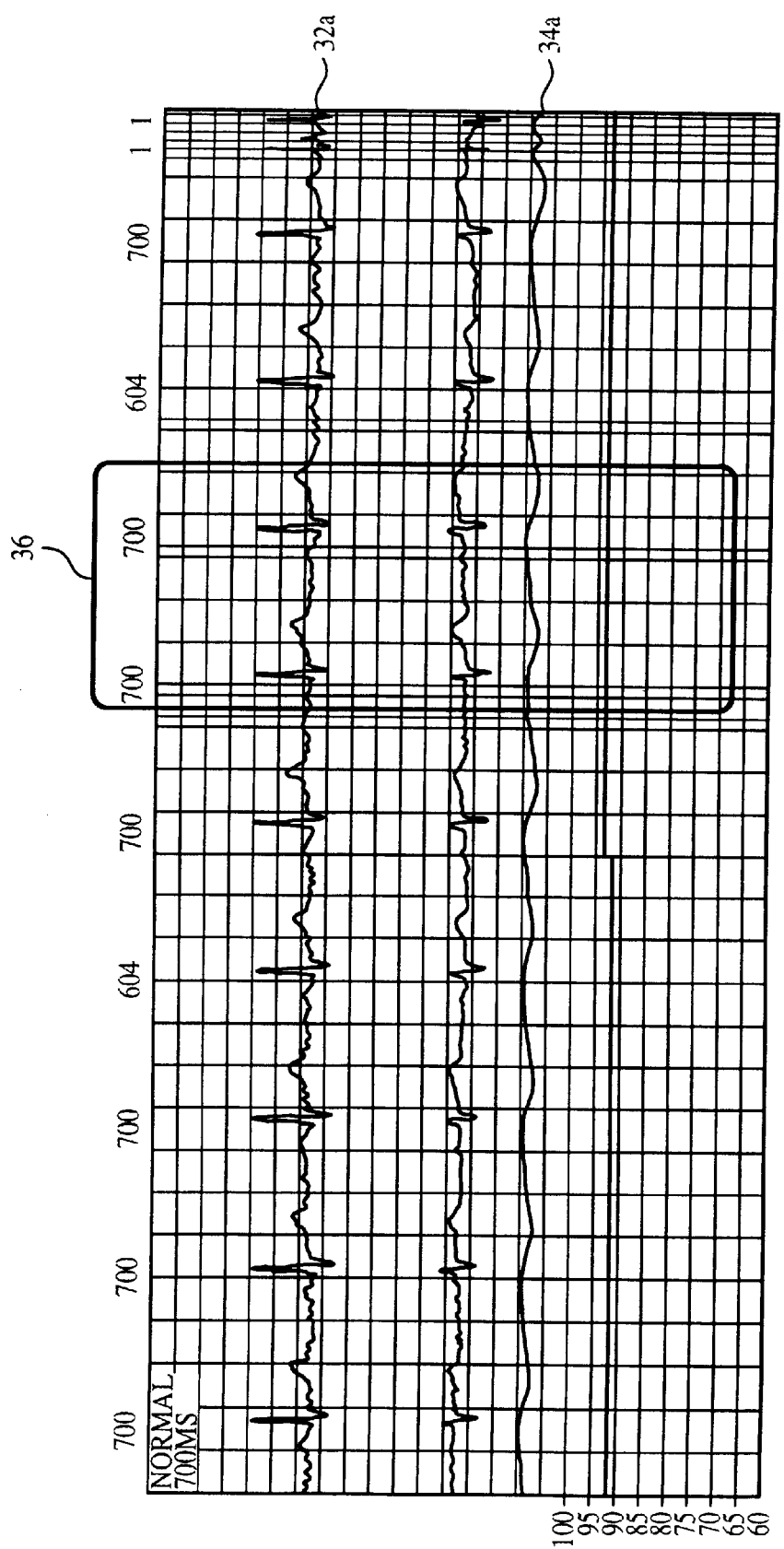
FIG. 3 is a graph showing normal recorded pulse oxymetry data signals.
Figure 4:
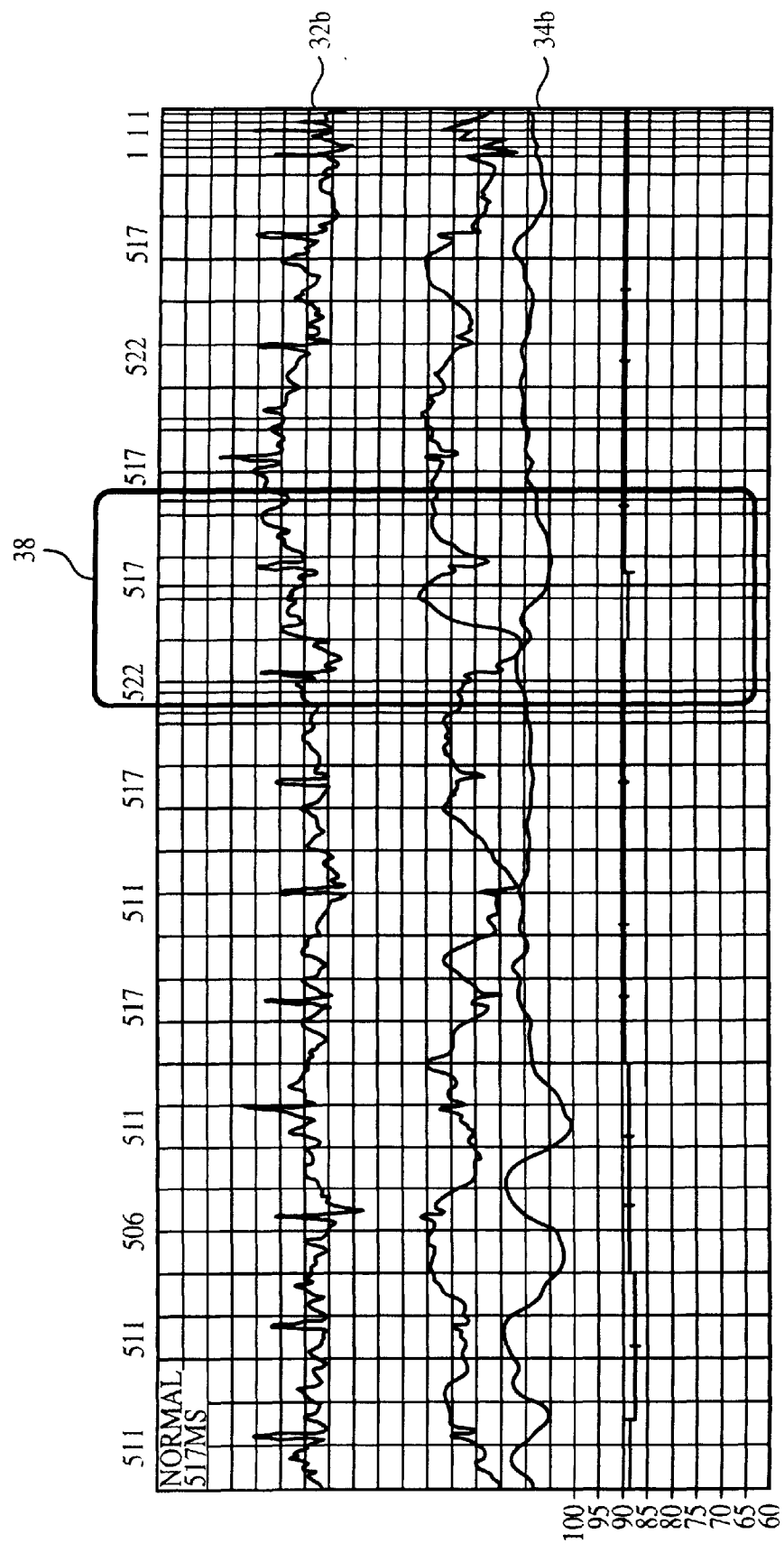
FIG. 4 is a graph showing invalid recorded pulse oxymetry data signals.

Referring to FIGS. 3–4, a pulse signal 32 (e.g., pulse signal 32a and pulse signal 32b) corresponds to a pulse oxymetry signal 34 (e.g., pulse oxymetry signal 34a and pulse oxymetry signal 34b). In box 36, pulse oxymetry waveform 34a is valid because successive oxymetry waveforms are correlated. In box 38, successive oxymetry waveforms are not correlated.

Process 10 records (12) the ECG and saturation data signals. In this embodiment an apparatus to record the signals is described in U.S. Pat. No. 6,125,296 ("'296" patent) and incorporated herein. Process 10 stores (14) the data signals in a removable memory (see '296 patent). Process 10 reads (16) the stored data signals from the removable memory. In this embodiment, the removable memory is a memory card that is placed in a memory card reader and subsequently read.

Figure 5:
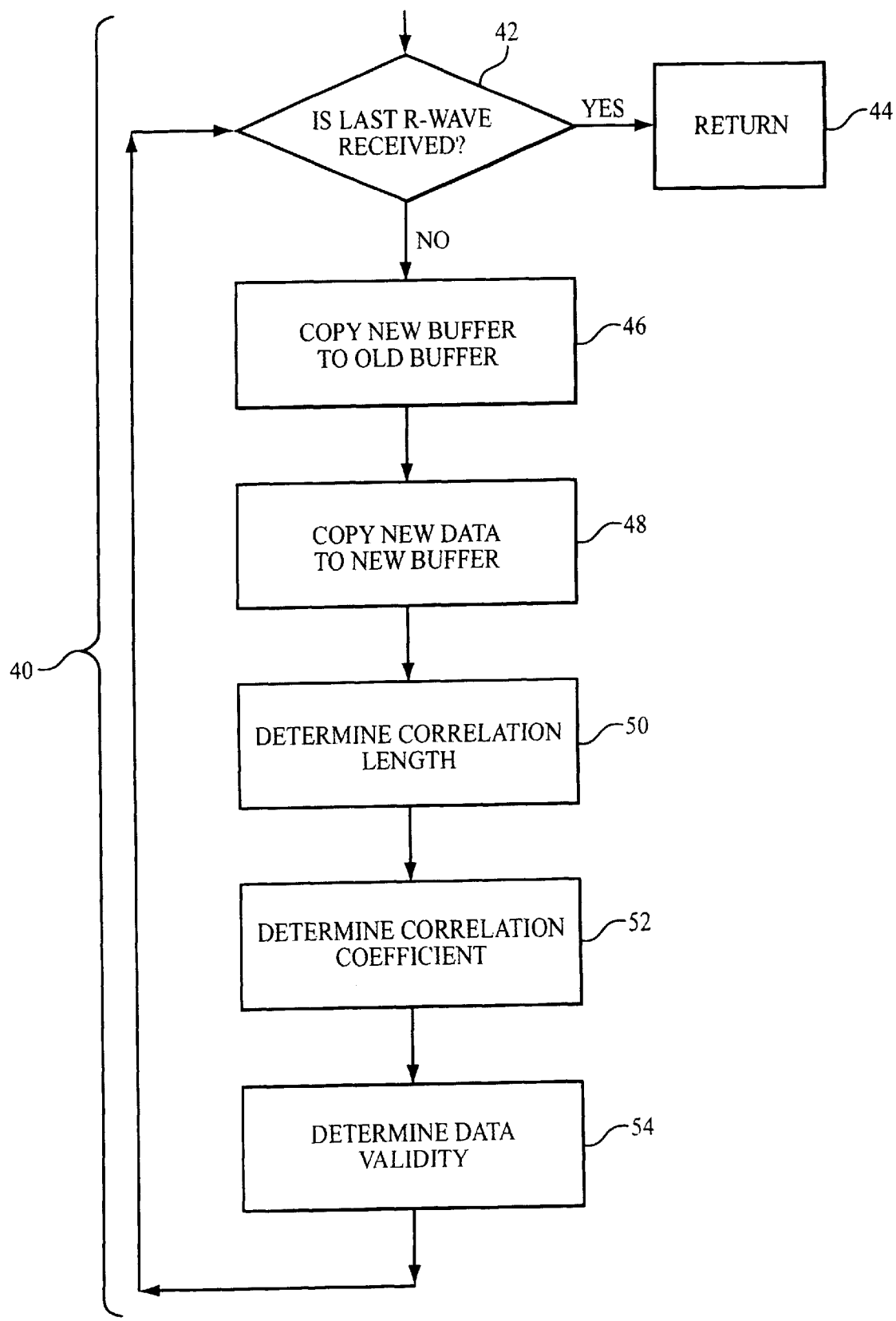
FIG. 5 is a flowchart of a process of detecting invalid pulse oxymetry data signals.

Referring to FIG. 5, process 10 determines (18) a correlation between successive pulse oxymetry waveforms by using a process 40. Process 40 uses a correlation coefficient to filter out invalid data signals. Process 40 receives the present R-wave, $R_n$, and determines (42) if the last R-wave has been received. If the last R-wave has been received, process 40 returns (44) to process 10 for further processing to determine the valid oxygen desaturation data signals (20). If more R-waves are present, process 40 copies (46) a previous segment of a pulse oxymetry waveform corresponding to the previous R-wave, $R_{n-1}$, and the R-wave previous to $R_{n-1}$, $R_{n-2}$, and a correlation length, $L_{n-1}$, from a new buffer to an old buffer. For each R-wave that is detected and is associated with a normal beat of sinus origin, process 40 copies (48) a segment of pulse oxymetry waveform corresponding to the present R-wave, $R_n$, and the previous R-wave, $R_{n-1}$, to the new buffer. Process 40 determines (50) a correlation length of the present segment, $L_n$, by comparing the pulse oxymetry waveforms in the new buffer to the old buffer. $L_n$ is determined by taking the smallest of: the time between $R_n$ and $R_{n-1}$, $R_{n-1}$ and $R_{n-2}$, and a constant equal to 0.4 times a sampling rate of 180 or a constant of 72. Process 40 stores $L_n$ in the new buffer. Process 40 determines (52) the cross correlation coefficient, $C_n$, as:

$$C_n = \Sigma((BUFN_m)(BUFO_m))/((\Sigma(BUFN_m)^2)(\Sigma(BUFO_m)^2))^{1/2}$$

for m=0, ... $LEN_{n-1}$ where BUFN are the pulse oxymetry waveform segment values in the new buffer, BUFO are the pulse oxymetry waveform segment values in the old buffer, and $LEN_{n-1}$ is the correlation length of the previous pulse oxymetry waveform segment. Process determines (54) the validity by comparing the cross correlation coefficient to the predetermined value. If more than a fraction of the correlation coefficients of normal beats, FRAC, in the last NS seconds of data have the $C_n$ less than a threshold value, $C_{th}$, then oxymetry data signals from $R_n$ to $R_{n-1}$ are invalid. In this embodiment, if more than 75% of the coefficients of normal beats in the last 6 seconds of data signals have the $C_n$ less than 0.9, then the oxymetry signals from $R_n$ to $R_{n-1}$ are invalid. The values of FRAC, NS, and $C_{th}$ are determined by the user. Again, process 40 determines if the last R-wave has been received (42).

Figure 6:
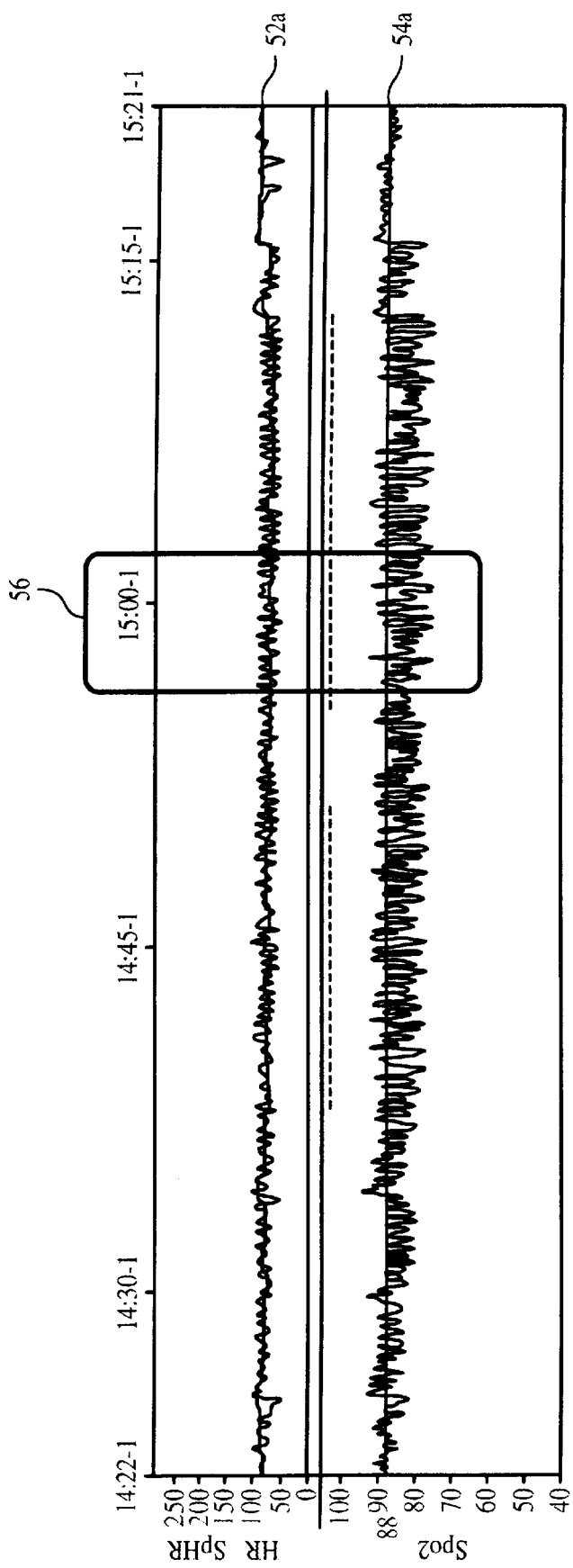
FIG. 6 is a graph showing valid recorded desaturation data signals.
Figure 7:
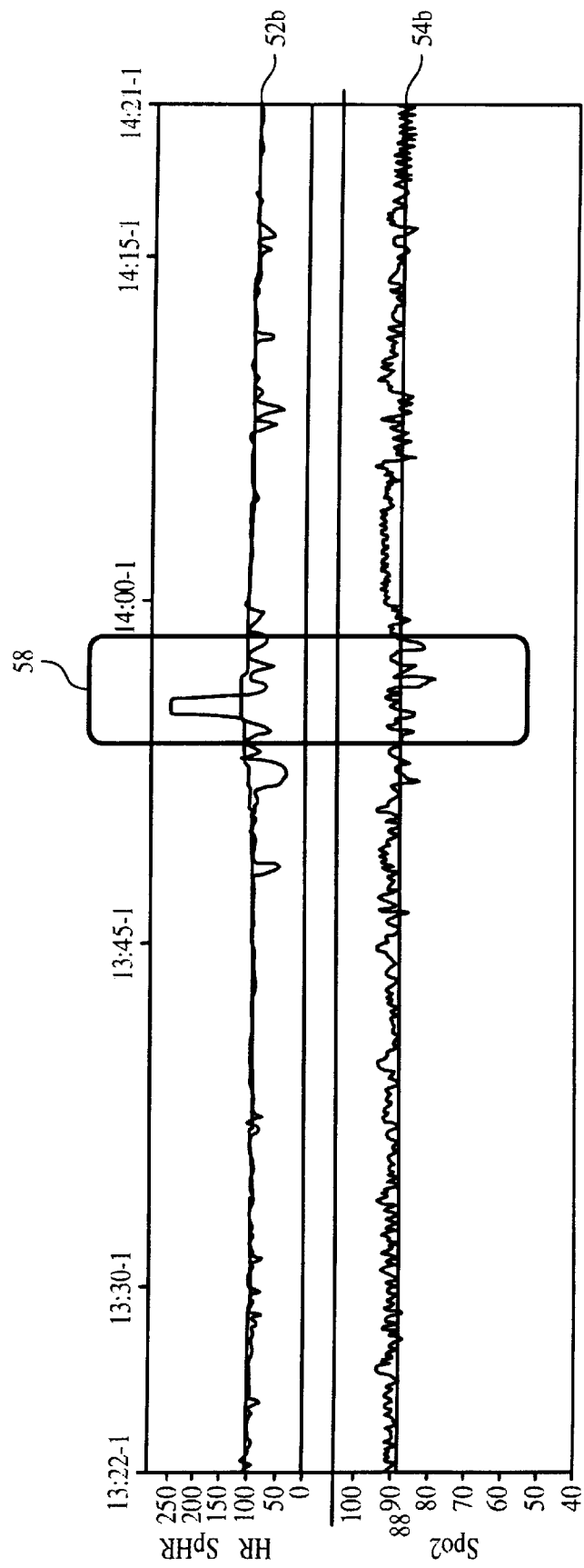
FIG. 7 is a graph showing invalid recorded desaturation data signals.

Referring to FIGS. 6–7, an EGG pulse signal 52 (e.g., ECG pulse signal 52a and ECG pulse signal 52b) is compared to an oxygen saturation signal 54 (i.e., oxygen saturation signal 54a and oxygen saturation signal 54b). In box 56, a valid oxygen saturation signal is shown because oxygen saturation signal 54a is correlated with ECG pulse signal 52a. In box 58, an invalid oxygen saturation data signal is shown because oxygen saturation signal 54b is not correlated with ECG pulse signal 52b.

Figure 8:
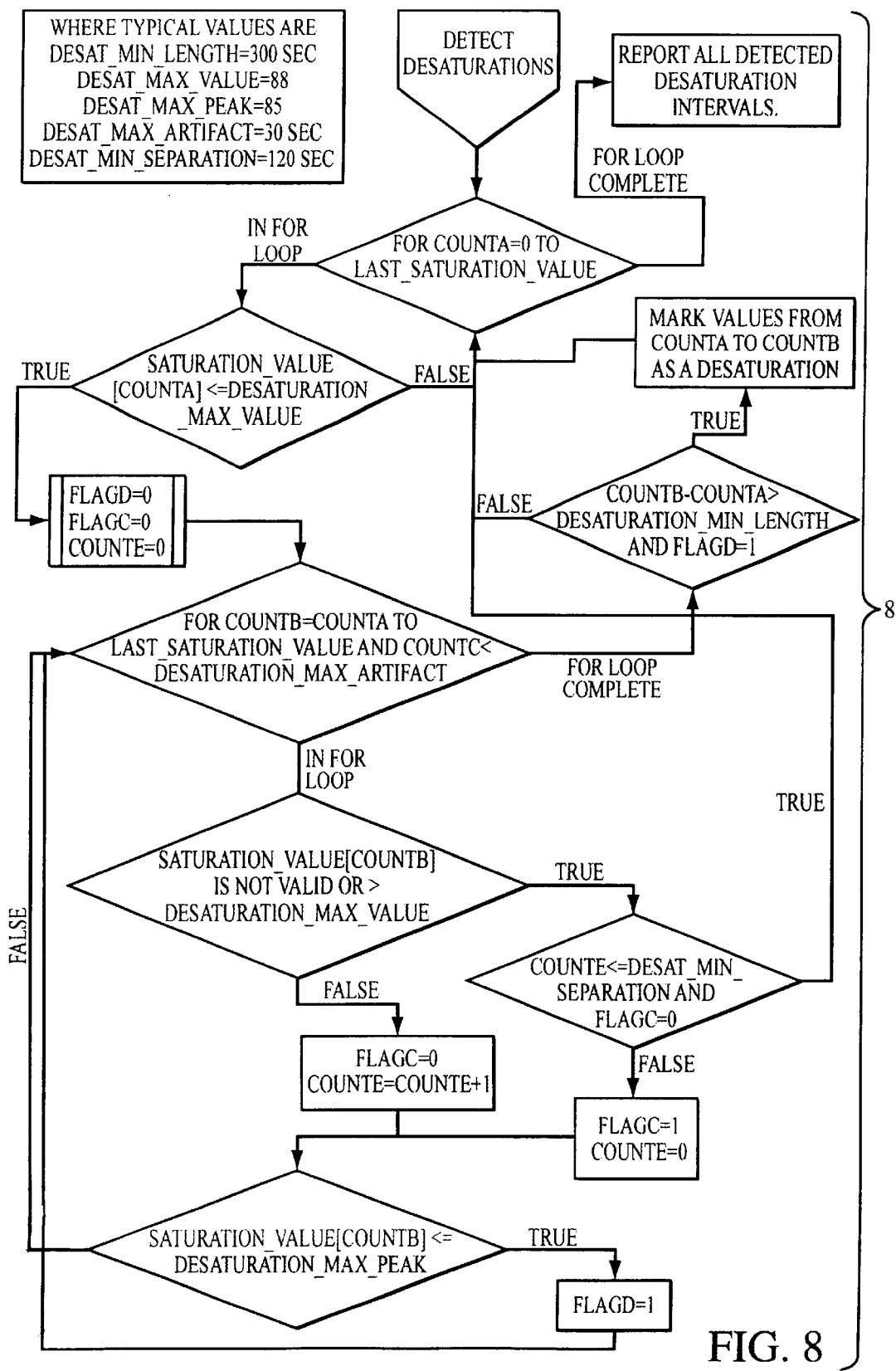
FIG. 8 is a flowchart of a process for detecting desaturation signals.

Referring to FIG. 8, process 80 determines from the valid data signals the true desaturation data signals. Process 80 finds those points in an oxygen saturation signals that are below a certain threshold, desat_max_value, for a minimum amount time, desat_min_length. However, process 80 allows for some values to be above desat_max_value. For example, a patient has desaturation signals for fifteen minutes but every minute there was an oxygen saturation signal above desat_max_value for a few seconds. The patient would still be considered physiologically in a desaturation mode for the entire 15 minutes. Process 80 uses a time artifact value, desat_max_artifact, to disregard these occurrences. Desat_max_artifact is the maximum amount of time that during desaturation process 80 will ignore values above desat_max_value. Process 80 also uses a desat_max_peak value to ignore values below desat_max_value that never reach desat_max_peak. Process 80 also uses a desat_min_separation value. The desat_min_separation value is the minimum time that is allowed between periods where the saturation value is above desat_max_value. Process 80 measures values from 0 to the last_saturation_value. In this embodiment, desat_max_value is 88%, desat_min_length is 300 seconds, desat_max_peak is 85%, desat_max_artifact is 30 seconds, and desat_min_separation is 120 seconds. In this embodiment, the values in process 80 can be set by a user.

One embodiment of the invention is realized in the following software code:

```
1.    if(open_file(&oxy_handle,"oxymin",OPEN_READ_NO_MESSAGE) &&
2.    filelength(oxy_handle) &&
3.    open_file(&oxy_pulse,"oxypulse.dat",OPEN_RANDOM) &&
4.    filelength(oxy_pulse) &&
5.    open_file(&beatstream, "beatstr",OPEN_READ)
6.    )
7.    {
8.    MEM_BEAT_STREAM_FILE_FORMAT bt{0,0,0},lbt;
9.    #define MAX_OXY_BUF ((SAMP_RATE*4)/10)
10.   #define OXY_BEATS_CHECKED (OXYMINUTE_5::SecPerOxy*5)
11.   struct
12.   {
13.     long offset;
14.     int artifact_detected;                //!=0 if aftifact detected
15.   }det_buf[OXY_BEATS_CHECKED];
16.   short mk[4]={80,80,-80,-80};
17.   short oxy_buf[MAX_OXY_BUF+4],last_oxy_buf [MAX_OXY_BUF+4];
18.   int sb,sc,coll_len;
19.   int oxymin_records;
20.   double sumx,sumy,sumxy,coll;
21.   OXYMINUTE_5 *ox_min_buf;
22.   int beat_cnt;
23.   memset(oxy_buf,0,sizeof(oxy_buf));
24.   beat_cnt=0;
25.   close(oxy_handle);
26. //            Printf("\n process oxy ");
27.   open_file(&oxy_handle, "oxymin",OPEN_RANDOM);
28.   oxymin_records=filelength(oxy_handle)/sizeof(OXYMINUTE_5);
29.   ox_min_buf=new OXYMINUTE_5[oxymin_records];
30.   lseek(oxy_handle,0,SEEK_SET);
31.   for (lb=0;lb<oxymin_records;lb++)
32.   {
33.   read(oxy_handle, (char*)&ox_min_buf [lb], sizeof(OXYMINUTE_5));
34.     ox_min _buf[lb].status&=~ (0x200 | 0x100);
35.   }
36.   while (!eof(beatstream))
37.   {
38.     lbt=bt;
39.     read(beatstream,&bt,sizeof(bt));
40. lseek(oxy_pulse, (lbt.offset+(SAMP_RATE/10)-4)*2,SEEK_SET);
41.     read(oxy_pulse,oxy_buf,MAX_OXY_BUF*2+8);
42.     coll_len=MIN(MAX_OXY_BUF,bt.offset-lbt.offset);
43.     sumx=0.0;
44.     sumy=0.0;
```

-continued

```
45.        sumxy=0.0;
46.        for (ia=4;ia<coll_len+4;ia++)
47.            {
48.                sb=oxy_buf[ia]-oxy_buf[4];
49.                sc=last_oxy_buf[ia]-last_oxy_buf[4];
50.                sumx+=sb*sb;
51.                sumy+=sc*sc;
52.                sumxy+=sb*sc;
53.                last_oxy_buf[ia]=oxy_buf[ia];
54.            }
55.        if (sumx * sumy >0.0)
56.            coll=sumxy/sqrt(sumx*sumy);
57.        else
58.            coll=0;
59. det_buf[beat_cnt%OXY_BEATS_CHECKED].offset=lbt.offset;
60. det_buf[beat_cnt%OXY_BEATS_CHECKED].artifact_detected=(coll
<0.9) && lbt.beat_label==BEAT_LABEL_NORMAL;
61.        sb=0;
62.        sc=0;
63.        for (ia=0;ia<OXY_BEATS_CHECKED;ia++)
64.            }
65.                if (det_buf[ia].offset>lbt.offset-
(SAMP_RATE*OXYMINUTE_5::SecPerOxy))
66.                    {
67.                        sb++;           //total count
68.    sc+=det_buf[ia].artifact_detected;
69.                    }
70.            }
71.        ia=lbt.offset/(SAMP_RATE*OXYMINUTE_5::SecPerOxy);
72.        lb=0;
73.        if (sc*4>sb*3 && ia>=0 && ia<oxymin_records)
74.            {
75.                ox_min_buf[ia].status|=0x200;
76.//               Printf(" ARTIFACT %5d sc %2d sb %2d",ia,sc,sb);
77.                lb=1;
78.            }
79.#if 0
80.lseek(oxy_pulse,(lbt.offset+(SAMP_RATE/10)-4)*2,SEEK_SET);
81.        if (lb)
82.            sb=oxy_buf[0]-100;
83.        else
84.            if (coll>0.9)
85.                sb=oxy_buf[0]+100;
86.            else
87.                sb=oxy_buf[0]+50;
88.        oxy_buf[1]=sb;
89.        oxy_buf[2]=sb;
90.        oxy_buf[3]=sb;
91.        write(oxy_pulse,oxy_buf,8);
92.        if (DEBUG_ART_DESAT)
93.            if ((beat_cnt%100)==0)
94.                for (ia=0;ia<coll_len;ia++)
95.                    Printf(" %3d",oxy_buf[ia]);
96. #endif
97.        beat_cnt++;
98.    }
99.if (DEBUG_ART_DESAT)
100.           Printf("\n look for desats for %d records thresh
%d %d %d %d ",oxymin_records,
101.           c_i.desat_spo2_thresh,
102.           c_i.artifact_desat_skip,
103.           c_i.desat_spo2_min _thresh,
104.   c_i.desat_min length);
105.           for (ia=0;ia<oxymin_records;ia++)
106.               {
107. if (DEBUG_ART_DESAT)
108. if (ia<400)Printf(" %d",ox_min _buf[ia].spo2_max);
109.               if ((ia&15)==0)
110.                   StatusPrintf("Oxy
%s",time___to string(ia*OXYMINUTE_5::SecPerOxy*SAMP_RATE));
111. if (DEBUG_ART_DESAT)
112.               Printf("\n at %3d %s %2d %2d %d %d",
113.               ia,
114.   time_to_string(ia*OXYMINUTE_5::
SecPerOxy*SAMP_RATE+c_i.base_time),
115.               ox_min _buf[ia].spo2_min,
116.               ox_min _buf[ia].spo2_max,
117.               ox_min buf[ia].OxyArtifact(),
118.               (ox_min _buf[ia].status&0x100) !=0)
```

```
-continued 119.    if (ox_min_buf[ia].spo2_max<=c_i.desat_spo2_thresh)
120.            {
121.            if (DEBUG_ART_DESAT)
122.                Printf(" start desat ");
123.            int term_loop;
124.            for
(lb=ia, lc=0, ld=0, le=0, term_loop=0;lb<oxymin_records   &&
(lc<(c_i.artifact_desat_skip/OXYMINUTE_5::SecPerOxy))   &&
!term_loop;lb++)
125.                {
126.                if (ox_min _buf[lb].OxyArtifact( ) ||
ox_min_buf[lb].spo2_max>c_i.desat_spo2_thresh)
127.                    {
128.                    if
(le<=c_i.artifact_desat_min separation/OXYMINUTE_5::SecFerOxy
&& !lc)
129.                        term_loop=1;
130.                    lc++;
131.                    le=0;
132.                    }
133.                else
134.                    {
135.                    lc=0;
136.                    le++;
137.                    }
138.    if (ox_min_buf[lb].spo2_min<=c_i.desat_spo2_min thresh)
139.                    ld++;
140.                }
141.            lb-=lc;
142.            if (DEBUG_ART_DESAT)
143.                Printf(" check lb-ia %d ld %d lc %d
le %d term %d",lb-ia,ld,lc,le,term_loop);
144.            if (((ib-
ia)>(c_i.desat_min _length/OXYMINUTE_5::SecPerOxy)) && ld)
145.                {
146.                if (DEBUG_ART_DESAT)
147.                    Printf(" DESAT IT ");
148.                for (lc=ia; lc<lb; lc++)
149.    ox_min_buf[lc].status|=0x100;                        }
150.            }
151.        }
152.        lseek(oxy_handle,0,SEEK SET);
153.        for (lb=0;lb<oxyminn_records;lb++)
154.    write(oxy_handle, (char*)&ox_min _buf[lb],
sizeof(OXYMINUTE_5));
155.        delete [ ] (ox_min_buf);
156.        close (beatstream);
157.        close(oxy_pulse);
158.        close(oxy_handle);
159.    if (((la=(clock( )-start_clock)) >0) && start_clock)
160.        Printf(" time at end of oxy art %g",la/CLK_TCK);
161.        }
```

Figure 9:
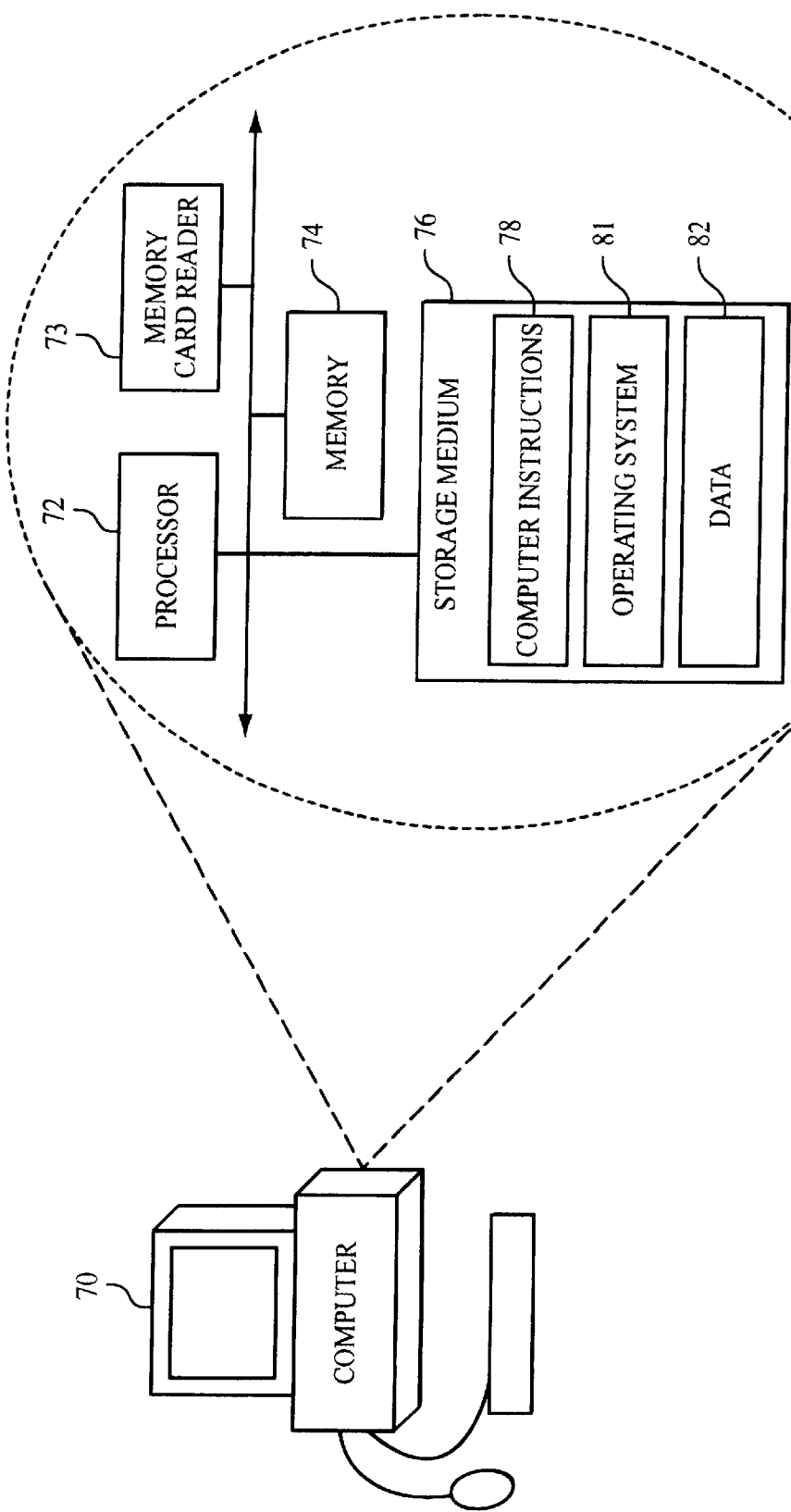
FIG. 9 is a block diagram of a computer system on which the process of FIG. 1 may be implemented.

Referring to FIG. 9, a computer 70 includes a processor 72 for processing oxymetry data signals stored on a memory card (not shown) and read by memory card reader 73. Computer 70 also includes a memory 74, and a storage medium 56 (e.g., hard disk). Storage medium 76 stores operating system 81, data signals 82, and computer instruction signals 78 which are executed by processor 72 out of memory 74 to perform process 10. In this embodiment, the memory card is a Personal Computer Memory Card (International Association) (PCMCIA) which is compatible with the Advanced Technology Attachment (ATA) interface standard, and memory reader 73 is manufactured by Sandisk of Sunnyvale, Calif. In one embodiment, computer instructions include executable instruction signals.

Process 10 is not limited to use with the hardware and software of FIG. 9; process 10 may find applicability in any computing or processing environment and with any type of machine that is capable of running a computer program. Process 10 may be implemented in hardware, firmware, software, or a combination of two or more. Process 10 may be implemented in computer programs executed on programmable computers/machines that each include a processor, a storage medium/article of manufacture readable by the processor (including volatile and non-volatile memory and/or storage elements), at least one input device, and one or more output devices. Program code may be applied to data entered using an input device to perform process 10 and to generate output information.

Each such program may be implemented in a high level procedural or objected-oriented programming language to communicate with a computer system. However, the programs can be implemented in assembly or machine language. The language may be a compiled or an interpreted language. Each computer program may be stored on a storage medium (article) or device (e.g., CD-ROM, hard disk, read only memory (ROM) integrated circuit, or magnetic diskette) that is readable by a general or special purpose programmable computer for configuring and operating the computer when the storage medium or device is read by the computer to perform process 10. Process 10 may also be implemented as a machine-readable storage medium, configured with a computer program, where upon execution, instructions in the computer program cause the computer to operate in accordance with process 10.

In other embodiments, process 10 can be performed using a processor located on a patient. In still other embodiments, the recorder can perform process 10. The invention is not limited to a specific location. Process 10 can be performed by a device connected to the patent, at the recorder, or anywhere external to the patient.

The invention is not limited to the specific embodiments described herein. The invention is not limited to the specific processing order of FIGS. 1, 5, and 8. Rather, the blocks of FIGS. 1, 5, and 8 may be re-ordered, as necessary, to achieve the results set forth above.

Other embodiments not described here are also within the scope of the following claims.

What is claimed is:

1. A method for processing pulse oxymetry data signals, comprising:
   recording pulse oxymetry data signals. the pulse oxymetry data signals having a plurality of oxymetry waveforms, the pulse oxymetry data signals corresponding to oxygen saturation data signals;
   determining a correlation coefficient between sequential oxymetry waveforms; and
   identifying a valid pulse oxymetry waveform;
   wherein determining the correlation coefficient comprises:
      storing a first pulse oxymetry waveform segment having a first length in a first buffer;
      copying said first pulse oxymetry waveform segment from said first buffer to a second buffer;
      copying a second pulse oxymetry waveform segment having a second length to said first buffer;
      comparing the first length, the second length and a predetermined value; and
      determining a correlation length related to said first and second lengths and said predetermined value.

2. The method of claim 1, wherein determining a correlation length comprises taking the minimum of the first length, the second length, and the predetermined value.

3. The method of claim 1, wherein determining a correlation coefficient comprises:
   determining a correlation coefficient from the first pulse oxymetry waveform segment and the second pulse oxymetry waveform segment;
   comparing the correlation coefficient to a threshold value; and
   filtering out an invalid pulse oxymetry waveform segment that has a correlation coefficient below the threshold value.

4. The method of claim 3, wherein filtering out the invalid pulse oxymetry waveform segment comprises eliminating pulse oxymetry waveform segments if 75% of the correlation coefficients for the last 6 seconds are above the threshold value of 0.9.

5. The method of claim 1, further comprising determining valid oxygen desaturation data signals.

6. The method of claim 5, wherein determining valid desaturation signals comprises labeling oxygen saturation signals below a threshold value for a predetermined time as valid desaturation data.

7. The method of claim 6, wherein the threshold value is 88% oxygen saturation and the predetermined time is 300 seconds.

8. The method of claim 6, wherein determining valid desaturation signals comprises eliminating artifacts.

9. The method of claim 6, wherein determining valid desaturation signals comprises ignoring desaturation signals below the threshold value that do not reach a peak value.

10. An apparatus for processing pulse oxymetry data signals, comprising:
    a memory that stores executable instruction data signals; and
    a processor that executes the instruction data signals to:
       record the pulse oxymetry data signals, the pulse oxymetry data signals having a plurality of oxymetry waveforms, the pulse oxymetry data signals corresponding to oxygen saturation data signals;
       determine a correlation coefficient between sequential oxymetry waveforms; and
       identify an valid pulse oxymetry waveform;
    wherein to determine the correlation coefficient comprises:
       storing a first pulse oxymetry waveform segment having a first length in a first buffer;
       copying said first pulse oxymetry waveform segment from said first buffer to a second buffer;
       copying a second pulse oxymetry waveform segment having a second length to said first buffer;
       comparing the first length, the second length and a predetermined value; and
       determining a correlation length related to said first and second lengths and said predetermined value.

11. The apparatus of claim 10, wherein determining a correlation length comprises taking the minimum of the first length, the second length, and the predetermined value.

12. The apparatus of claim 10, wherein to determine a correlation coefficient comprises:
    determining a correlation coefficient from the first pulse oxymetry waveform segment and the second pulse oxymetry waveform segment;
    comparing the correlation coefficient to a threshold value; and
    filtering out an invalid pulse oxymetry waveform segment, the invalid pulse oxymetry waveform segment having correlation coefficient below the threshold value.

13. The apparatus of claim 12, wherein filtering out the invalid pulse oxymetry waveform segment comprises eliminating pulse oxymetry waveform segments if 75% of the correlation coefficients for the last 6 seconds are above the threshold value of 0.9.

14. The apparatus of claim 10, further comprising instruction data signals to determine valid oxygen desaturation data signals.

15. The apparatus of claim 14, wherein to determine valid desaturation signals comprises labeling oxygen saturation signals below a threshold value for a predetermined time as valid desaturation data.

16. The apparatus of claim 15, wherein the threshold value is 88% oxygen saturation and the predetermined time is 300 seconds.

17. The apparatus of claim 15, wherein to determine valid desaturation signals comprises eliminating artifacts.

18. The apparatus of claim 15, wherein to determine valid desaturation signals comprises ignoring desaturation signals below the threshold value that do not reach a peak value.

19. An article comprising a machine-readable medium that stores executable instruction signals for processing pulse oxymetry data signals, the instruction signals causing a machine to:
    record the pulse oxymetry data signals, the pulse oxymetry data signals having a plurality of oxymetry waveforms, the pulse oxymetry data signals corresponding to oxygen saturation data signals;

determine a correlation coefficient between sequential oxymetry waveforms; and identify a valid pulse oxymetry waveform;

wherein to determine the correlation coefficient comprises:

storing a first pulse oxymetry waveform segment having a first length in a first buffer;

copying said first pulse oxymetry waveform segment from said first buffer to a second buffer;

copying a second pulse oxymetry waveform segment having a second length to said first buffer;

comparing the first length, the second length and a predetermined value; and determining a correlation length related to said first and second lengths and said predetermined value.

20. The article of claim 19, wherein determining a correlation length comprises taking the minimum of the first length, the second length, and the predetermined value.

21. The article of claim 19, wherein to determine a correlation coefficient comprises:

determining a correlation coefficient from the first pulse oxymetry waveform segment and the second pulse oxymetry waveform segment;

comparing the correlation coefficient to a threshold value; and filtering out an invalid pulse oxymetry waveform segment, the invalid pulse oxymetry waveform segment having correlation coefficient below the threshold value.

22. The article of claim 21, wherein filtering out the invalid pulse oxymetry waveform segment comprises eliminating pulse oxymetry waveform segments if 75% of the correlation coefficients for the last 6 seconds are above the threshold value of 0.9.

23. The article of claim 21, further comprising instruction signals causing a machine to:

determine valid oxygen desaturation data signals.

24. The article of claim 23, wherein to determine valid desaturation signals comprises labeling oxygen saturation signals below a threshold value for a predetermined time as valid desaturation data.

25. The article of claim 24, wherein the threshold value is 88% oxygen saturation and the predetermined time is 300 seconds.

26. The article of claim 24, wherein to determine valid desaturation signals comprises eliminating artifacts.

27. The article of claim 24, wherein to determine valid desaturation signals comprises ignoring desaturation signals below the threshold value that do not reach a peak value.

* * * * *